US008471057B2

(12) United States Patent
Zhu et al.

(10) Patent No.: US 8,471,057 B2
(45) Date of Patent: Jun. 25, 2013

(54) SITAGLIPTIN INTERMEDIATES, PREPARATION METHODS AND USES THEREOF

(75) Inventors: Guoliang Zhu, Zhejiang (CN); Jian Zhang, Zhejiang (CN); Lijun Yang, Zhejiang (CN); Qingdan Yao, Zhejiang (CN); Jie Ying, Zhejiang (CN)

(73) Assignee: Zhejiang Jiuzhou Pharmaceutical Co., Ltd. (CN)

( * ) Notice: Subject to any disclaimer, the term of this patent is extended or adjusted under 35 U.S.C. 154(b) by 0 days.

(21) Appl. No.: 13/497,874

(22) PCT Filed: Sep. 25, 2010

(86) PCT No.: PCT/CN2010/077262
§ 371 (c)(1),
(2), (4) Date: Mar. 23, 2012

(87) PCT Pub. No.: WO2011/035725
PCT Pub. Date: Mar. 31, 2011

(65) Prior Publication Data
US 2012/0178957 A1    Jul. 12, 2012

(30) Foreign Application Priority Data
Sep. 27, 2009   (CN) .......................... 2009 1 0153059

(51) Int. Cl.
*C07C 69/035* (2006.01)
(52) U.S. Cl.
USPC ....................................................... 560/103
(58) Field of Classification Search
USPC ....................................................... 560/103
See application file for complete search history.

(56) References Cited

FOREIGN PATENT DOCUMENTS

| CN | 1761642 A | 4/2006 |
|---|---|---|
| CN | 101417999 A | 4/2009 |
| WO | 2004/087650 A2 | 10/2004 |

OTHER PUBLICATIONS

Dooseop Kim et al., Triazolopiperazine-amides as dipeptidyl peptidase IV inhibitors: Close analogs of JANUVIA™ (sitagliptin phosphate), Bioorganic & Medicinal Chemistry Letters 17 (2007), 3373-3377.

Karl B. Hansen et al., "First Generation Process for the Preparation of the DPP-IV Inhibitor Sitagliptin," Oganic Process Research & Development, 2005, 9, 634-639.
Gui-fang Sun et al., "Graphical Synthetic Routes of Sitagliptin," Chinese Journal of Pharmaceuticals, 2008, 39(5), 383-386. [English Summary].
Kim, D. et al., "(2R)-4-Oxo-4-[3-(Trifluoromethyl)-5,6-dihydro[1,2,4]triazolo[4,3-a]pyrazin-7(8H)-yl]-1-(2,4,5-trifluorophenyl)butan-2-amine: A Potent, Orally Active Dipeptidyl Peptidase IV Inhibitor for the Treatment of Type 2 Diabetes," Journal of Medicinal Chemistry (J. Med. Chem.), 2005, VII, 48, 141-151.

*Primary Examiner* — Wu-Cheng Winston Shen
*Assistant Examiner* — Karen Cheng
(74) *Attorney, Agent, or Firm* — Blank Rome LLP

(57) ABSTRACT

The present invention relates to Sitagliptin intermediate and preparation method and use thereof. The method comprises reacting compound of formula (II) and trifluorobromobenzene with a Grignard reagent by a Grignard reaction to obtain a compound of formula (I). Compound of formula (I) is a new intermediate compound for the synthesis of Sitagliptin. Compound of formula (I) can be easily used for preparing another important intermediate compound of formula (V) for the synthesis of Sitagliptin. The structures of the compounds mentioned above are as the following:

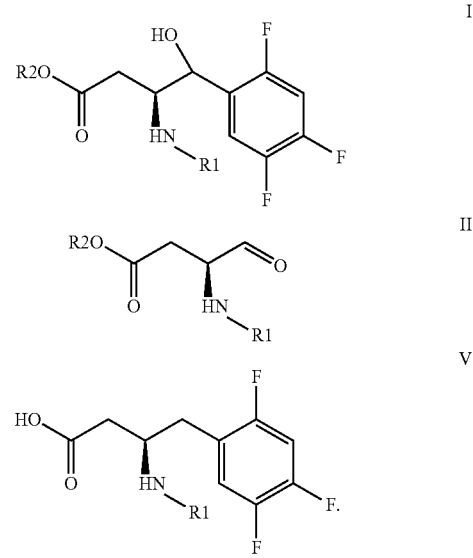

13 Claims, No Drawings

SITAGLIPTIN INTERMEDIATES, PREPARATION METHODS AND USES THEREOF

REFERENCE TO RELATED APPLICATION

The present application is a national stage of PCT/CN2010/077262, filed Sep. 25, 2010, which claims priority to Chinese patent application No. 200910153059.3 filed Sep. 27, 2009, titled "Sitagliptin intermediate and a preparation method and use thereof", the entire contents thereof are incorporated by reference as a whole.

FIELD OF THE INVENTION

The present invention relates to the field of chemical synthesis, in particular to Sitagliptin intermediates and preparation methods and uses thereof.

BACKGROUND OF THE INVENTION

The chemical name of Sitagliptin is (3R)-3-amino-1-[3-(trifluoromethyl)-5,6,7,8-tetrahydro-1,2,4-triazolo[4,3-a]pyrazin-7-yl]-4-(2,4,5-trifluorophenyl)butan-1-one, whose structure is of formula 1:

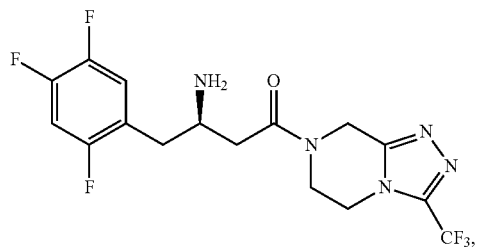

Sitagliptin is a dipeptidyl peptidase-IV (DPP-IV) inhibitor, and used to treat type II diabetes in clinic.

At present, the methods for preparing Sitagliptin are as follows:

Route I (Reference Document 1): (2R)-4-Oxo-4-[3-(Trifluoromethyl)-5,6-dihydro[1,2,4]triazolo[4,3-a]pyrazin-7(8H)-yl]-1-(2,4,5-trifluorophenyl)butan-2-amine: A Potent, Orally Active Dipeptidyl Peptidase IV Inhibitor for the Treatment of Type 2 Diabetes, Journal of Medicinal Chemistry (J. Med. Chem.), 2005, V11, 48, 141-151, Kim D, et al):

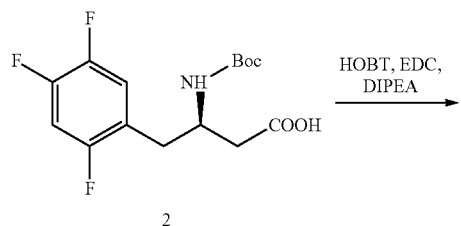

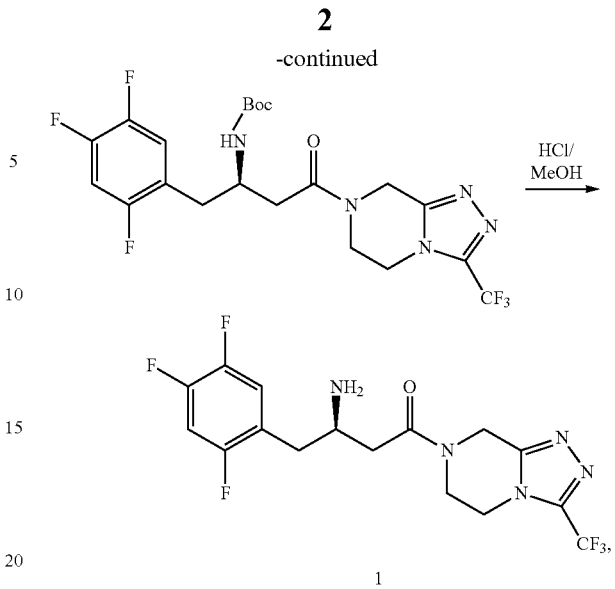

wherein -Boc group is tert-butoxycarbonyl. HOBT is 1-hydroxybenzotriazole, EDC is 1,2-dichloroethane, DIPEA is N,N-diisopropyl ethylamine (these groups or abbreviations thereof have the same definitions at each occurrence in structure formula and the description hereinafter).

Route II (Reference Document 2): WO 2004087650, publication date: Oct. 14, 2004, Applicant: Merck & Co. INC.):

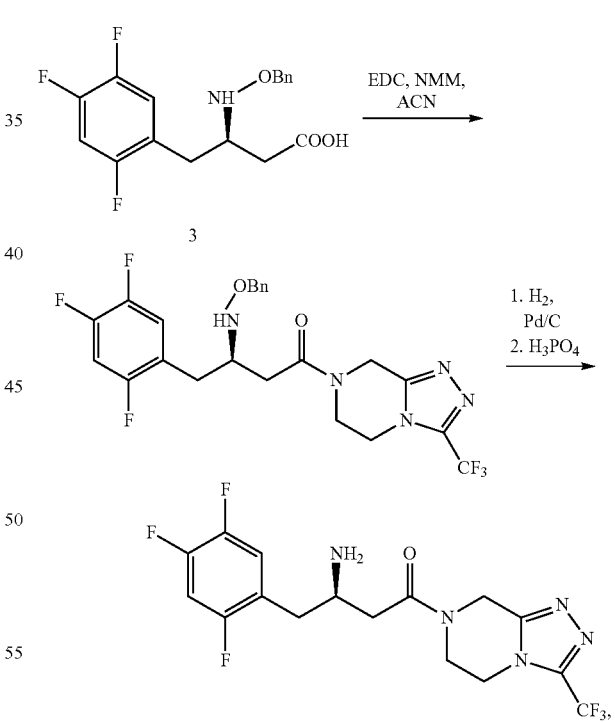

wherein —OBn group is benzyloxy. NMM is N-methyl morpholine, ACN is aminochloronaphthoquinone (these groups or abbreviations thereof have the same definitions at each occurrence in structure formula and the description hereinafter).

It can be seen that compound 2 ((R)-3-(tert-butoxycarbonylamino)-4-(2,4,5-trifluorophenyl)butyric acid) and compound 3 ((R)-3-(benzyloxyamino)-4-(2,4,5-trifluorophenyl) butyric acid) are important intermediates for preparation of sitagliptin.
Wherein, the synthetic route of the intermediate compound 2 is shown as below (see reference document 1):
The synthetic route of the intermediate compound 3 is shown as below (see reference document 2):
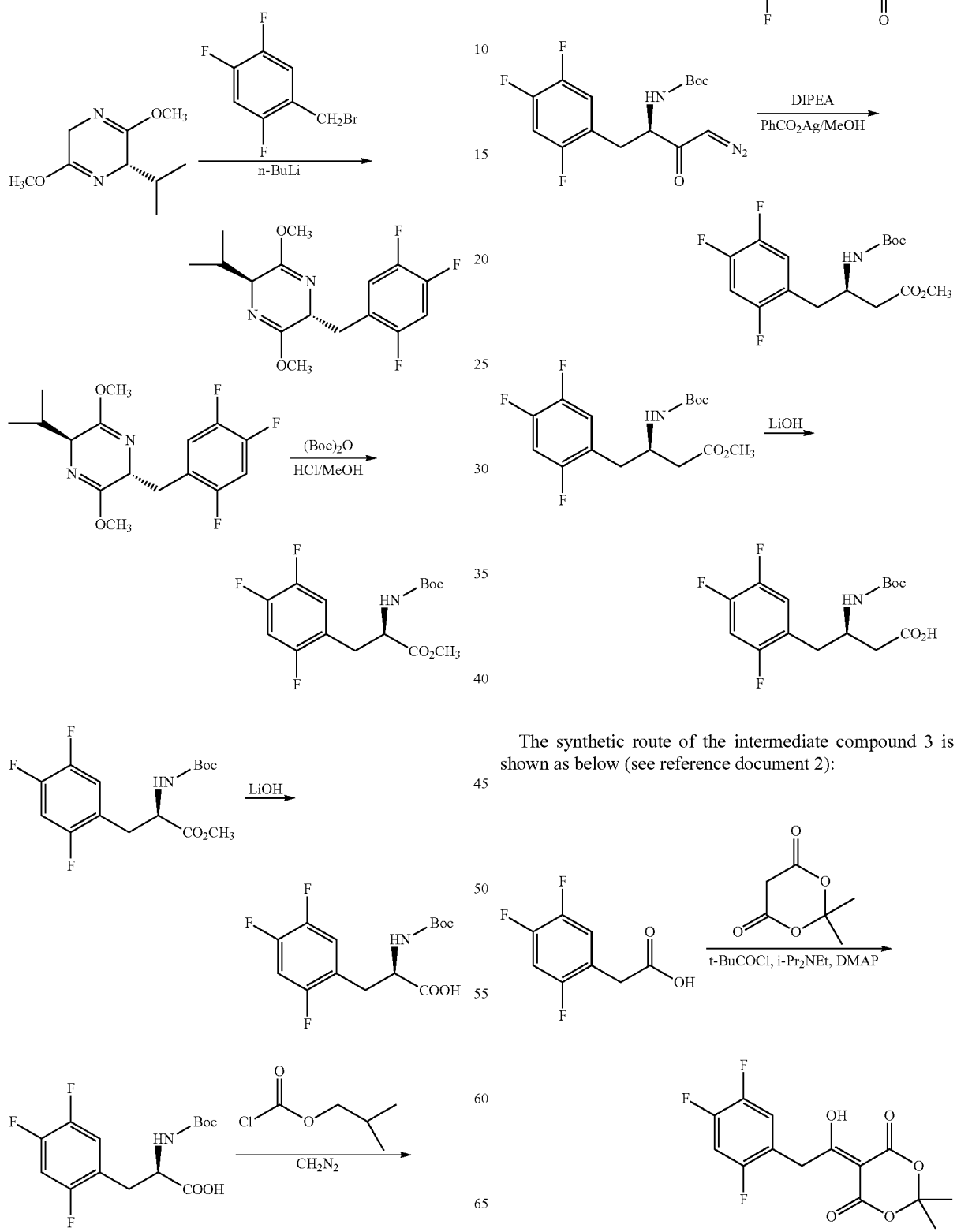

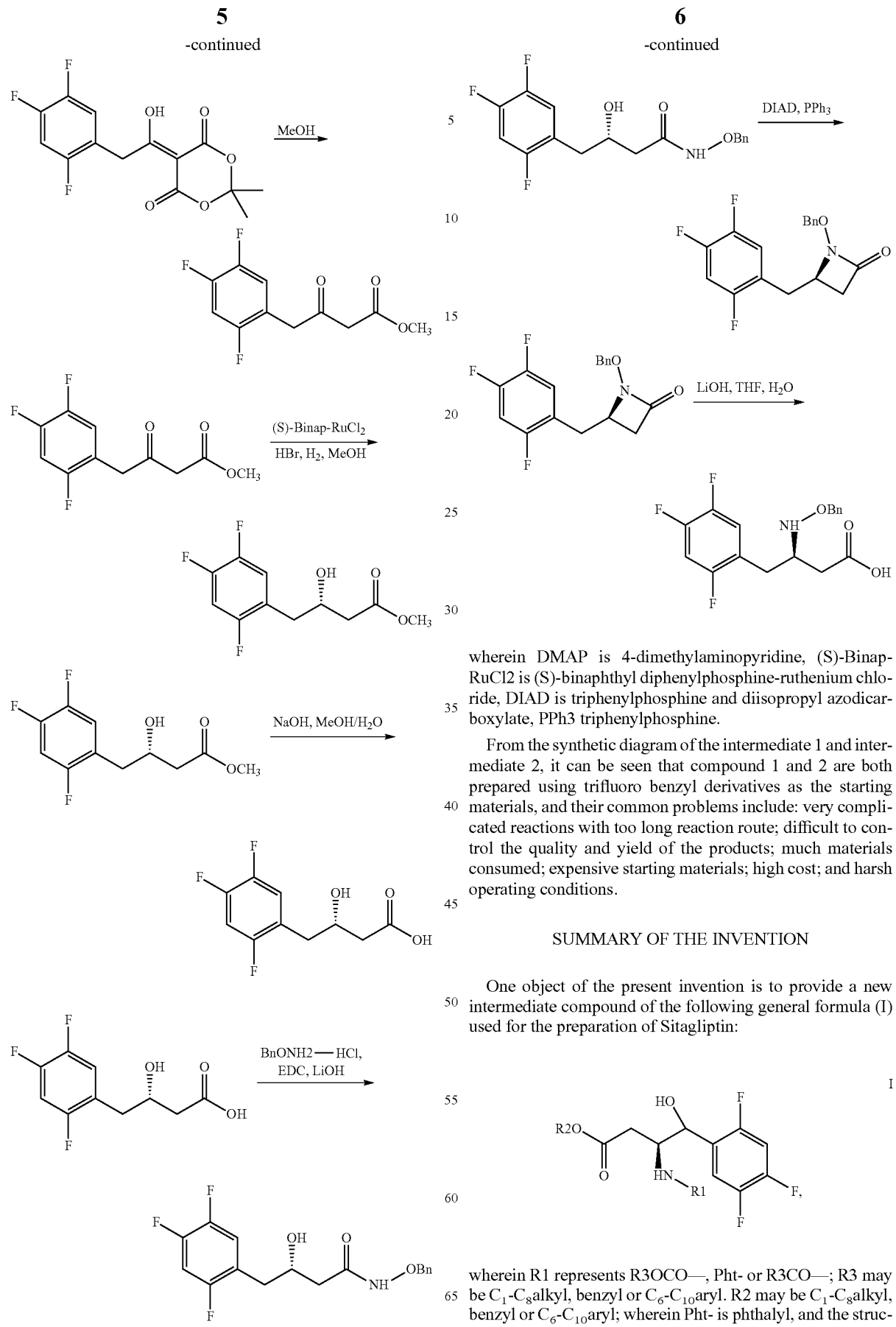

wherein DMAP is 4-dimethylaminopyridine, (S)-Binap-RuCl2 is (S)-binaphthyl diphenylphosphine-ruthenium chloride, DIAD is triphenylphosphine and diisopropyl azodicarboxylate, PPh3 triphenylphosphine.

From the synthetic diagram of the intermediate 1 and intermediate 2, it can be seen that compound 1 and 2 are both prepared using trifluoro benzyl derivatives as the starting materials, and their common problems include: very complicated reactions with too long reaction route; difficult to control the quality and yield of the products; much materials consumed; expensive starting materials; high cost; and harsh operating conditions.

SUMMARY OF THE INVENTION

One object of the present invention is to provide a new intermediate compound of the following general formula (I) used for the preparation of Sitagliptin:

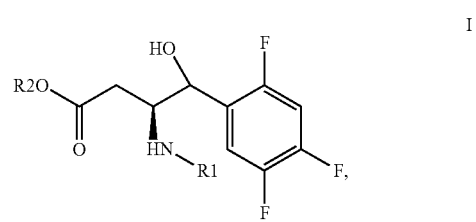

wherein R1 represents R3OCO—, Pht- or R3CO—; R3 may be $C_1$-$C_8$alkyl, benzyl or $C_6$-$C_{10}$aryl. R2 may be $C_1$-$C_8$alkyl, benzyl or $C_6$-$C_{10}$aryl; wherein Pht- is phthalyl, and the structure thereof is as shown in formula 4:

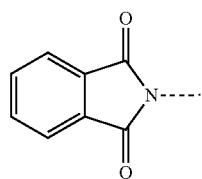

In preferred compounds of formula (I) provided in the present invention, R3 is tert-butyl, benzyl or phenyl, that is to say, R1 is tert-butoxycarbonyl, benzyloxycarbonyl or benzoyl; R2 is methyl, benzyl or cyclohexyl.

More preferred compounds of the present invention are selected from the groups consisting of:
methyl (3S)-3-(tert-butoxycarbonylamino)-4-hydroxy-4-(2,4,5-trifluorophenyl)butyrate;
benzyl (3S)-3-(tert-butoxycarbonylamino)-4-hydroxy-4-(2,4,5-trifluorophenyl)butyrate;
cyclohexyl (3S)-3-(tert-butoxycarbonylamino)-4-hydroxy-4-(2,4,5-trifluorophenyl)butyrate;
methyl (3S)-3-(benzyloxycarbonylamino)-4-hydroxy-4-(2,4,5-trifluorophenyl)butyrate; and
benzyl (3S)-3-(benzoylamino)-4-hydroxy-4-(2,4,5-trifluorophenyl)butyrate.

Another object of the present invention is to provide a method for preparing compound of formula (I), and the method is illustrated by chemical reaction as follows:

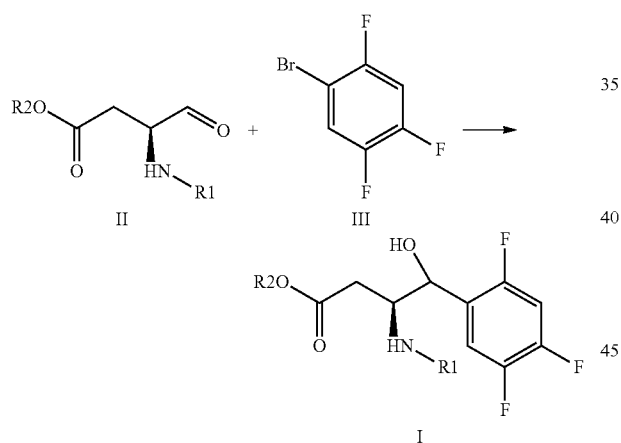

wherein R1 and R2 have the same definitions as defined above in the compound of formula (I).

The specific schemes are as follows:
Compound (II) and compound (III) (trifluorobromobenzene) as raw materials are reacted with a Grignard reagent in an organic solvent (solvent 1). After the completion of the Grignard reaction, layers are separated and extracted to obtain compound (I).

The Grignard reagent is (1) magnesium or lithium; (2) (R4)2Mg, R4Li or R4MgX;
wherein R4 represents $C_1$-$C_6$alkyl or $C_6$-$C_{10}$aryl, preferably methyl, ethyl, propyl, benzyl or phenyl; X is selected from chloro or bromo.

The Grignard reagent is more preferably magnesium, methyl magnesium bromide or benzyl lithium.

When magnesium or lithium is used, iodine is added to the reaction as an initiator.

The solvent 1 is selected from ethers (such as diethyl ether, tetrahydrofuran, methyl tetrahydrofuran or methyl tert-butyl ether), or (substituted) aromatic hydrocarbons (such as toluene or chlorobenzene); preferably ethers; most preferably tetrahydrofuran. The reaction temperature is −45 to 50° C. The reaction time is 0-48 hours. The molar ratio of compound (II) and trifluorobromobenzene is 1.0:(1.0-7.0).

A further object of the present invention is to provide a method for preparing compound of formula (V) from compound of formula (I), the method specifically comprises:
(1) compound of formula (IV) is prepared using compound of formula (I) as a raw material. Compound of formula (IV) can be used for the preparation of compound of formula (V) (an important intermediate for preparation of Sitagliptin). The specific route is as follows:

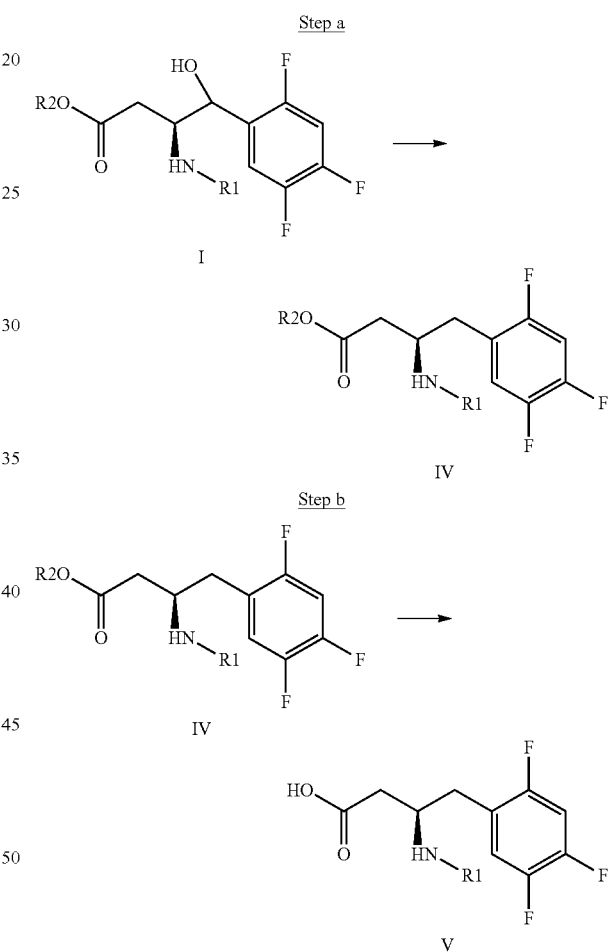

Wherein R1 and R2 have the same definitions as defined above in the compound of formula (I).

The specific schemes are as follows:
Step a: reacting compound of formula (I) with a catalyst in an organic solvent (solvent 2) to remove the heteroatom from the benzyl group, after the completion of the reaction, the mixture is filtered, concentrated under reduced pressure to give compound of formula (IV).

Wherein, the catalyst is palladium carbon or Raney nickel. The solvent 2 is selected from alcohol solvents, preferably methanol, ethanol, isopropanol, n-propanol or n-butanol, most preferably anhydrous ethanol or methanol. The reaction temperature is 0-100° C.; preferably 20-40° C. The reaction time is 0.5-48 hours, preferably 5-10 hours. Nitrogen gas is used in the reaction process for replacement. The pressure of hydrogen gas in the reaction is 0.1-10 Mpa, preferably 0.5-1.0 Mpa. The amount of solvent 2 is 2-20 times, preferably 5-10 times as that of compound (I) by weight. The weight ratio of the catalyst to compound (I) is (0.01-0.1): 1.0.

Step b: compound of formula (IV) is subjected to a hydrolysis reaction with an alkali to give compound of formula (V). The solvent used in the hydrolysis process is selected from water, or a mixed solvent of water and an organic solvent (solvent 3) selected from amides (such as N,N-dimethylformamide), alcohols (such as methanol, ethanol, isopropanol, n-propanol or n-butanol), (substituted) aromatic hydrocarbons (such as toluene or chlorobenzene), ethers (such as methyl t-butyl ether or tetrahydrofuran) or halogenated hydrocarbons (such as dichloromethane). The solvent 3 is preferably aromatic hydrocarbons, most preferably toluene. The alkali used may be sodium hydroxide, potassium hydroxide, potassium carbonate or sodium carbonate.

(2) Compound of formula (VI) is prepared using compound of formula (I) as a raw material. Compound of formula (VI) can be used for the preparation of a compound of formula (V) (an important intermediate for preparation of Sitagliptin). The specific route is as follows:

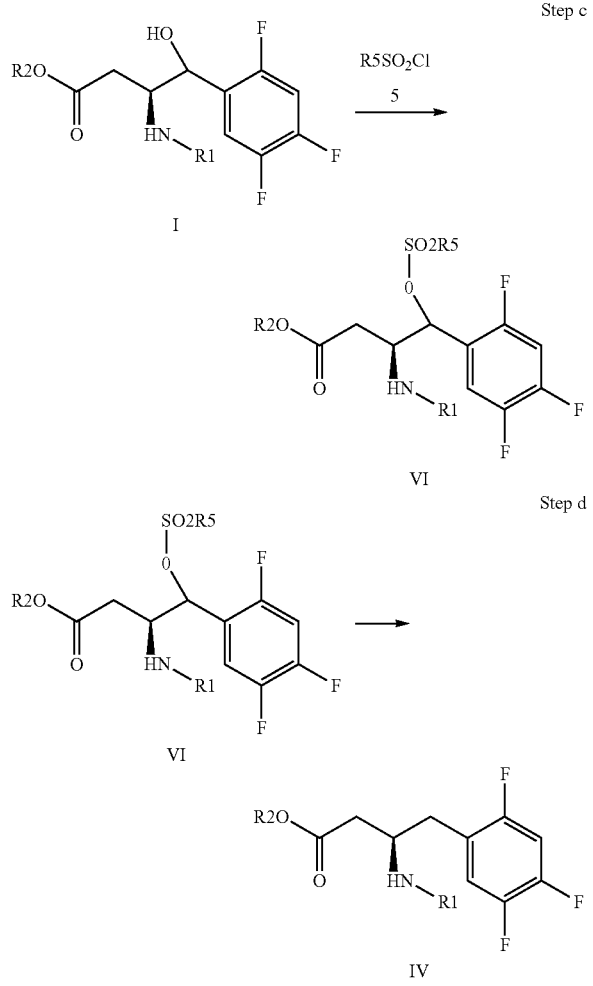

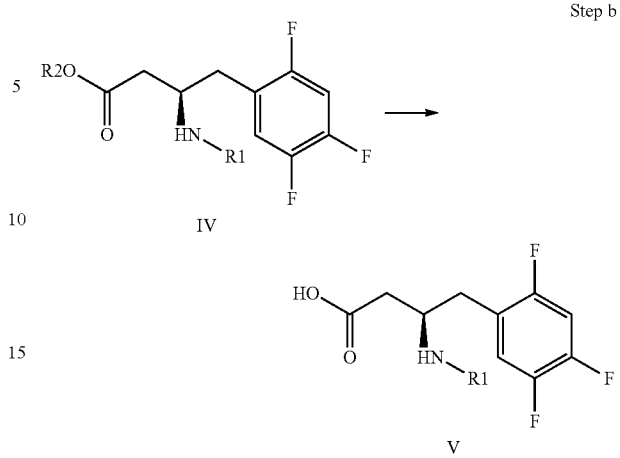

wherein R1 and R2 have the same definitions as defined above in the compound of formula (I);

R5 represents trifluoromethyl, $C_1$-$C_8$alkyl, phenyl or phenyl substituted on the para-position, wherein the substituent on para-position of the phenyl group may be H, Cl, Br, I, methyl, nitro or acetamido (AcNH—).

In the preferred compound 5 provided in the present invention, R5 is trifluoromethyl, methyl, ethyl, phenyl or p-tolyl, most preferably methyl or p-tolyl.

The specific schemes are as follows:

Step c: compound of formula (I) is esterificated with compound 5 in an organic solvent (solvent 4) to obtain a compound of formula (VI). The solvent 4 is selected from halogenated hydrocarbons (such as dichloromethane or chloroform), (substituted) aromatic hydrocarbons (such as toluene or chlorobenzene), ethers (such as tetrahydrofuran) or acetonitrile, preferably halogenated hydrocarbons, most preferably dichloromethane.

Step d: the reaction conditions and the operation for removing the sulfate group (—OSO2R5) are the same as those of step a, and both of them involve the reaction of removing the heteroatom from the benzyl group.

The purpose of esterifying the hydroxyl group on compound of formula (I) firstly is that the heteroatom on the benzyl group could be removed more easily.

The process for the preparation of compound of formula (IV) from compound of formula (V) is same as step b.

The method for preparing Sitagliptin using compound of formula (V) could be preformed according to the methods disclosed in reference document 1 and reference document 2 described in the background of the invention.

In the aspect of preparation of the intermediates for Sitagliptin, the present invention has the following advantages: short reaction routes; simple reactions; mild reaction conditions; easy to control the process and quality of the products; small amount of materials consumed; easily available and inexpensive starting materials (may be obtained from natural amino acids); low cost; and high yield and chiral purity of product, etc. Moreover, a new intermediate compound was obtained, thus, the method has high value in industrial application and economy.

DETAILED DESCRIPTION OF THE INVENTION

In order to understand the present invention better, now further illustration will be made in combination with the specific examples.

Preparation of New Intermediate Compound (I)

Example 1

Preparation of (3S)-methyl 3-(tert-butoxycarbonylamino)-4-hydroxy-4-(2,4,5-trifluorophenyl)butyrate 13.2 g metal magnesium and 400 ml tetrahydrofuran were added into a clean flask. 116.05 g trifluorobromobenzene was added thereto dropwise after initiation by iodine and the reaction was kept at 30-40° C. for 3 hours for use. 29.9 g (S)-methyl 3-(tert-butoxycarbonyl amino)-4-oxo-n-butyrate was dissolved in 300 ml THF, and cooled to −20° C. The solution mentioned above was added thereto dropwise over two hours and kept at the temperature for 3 hours. 400 ml ammonium chloride solution was added dropwise. Layers were separated. The aqueous layer was extracted with tetrahydrofuran. The organic layer was dried and concentrated to get 14.5 g (3S)-methyl 3-(tert-butoxy carbonylamino)-4-hydroxy-4-(2,4,5-trifluoromethyl-phenyl)butyrate (yield: 66%).

Example 2

Preparation of (3S)-benzyl 3-(tert-butoxycarbonylamino)-4-hydroxy-4-(2,4,5-trifluorophenyl)butyrate In accordance with the method described in Example 1, except that 30.7 g (S)-benzyl 3-(tert-butoxycarbonylamino)-4-oxo-n-butyrate was used to replace (S)-methyl 3-(tert-butoxycarbonylamino)-4-oxo-n-butyrate, 21.07 g (3S)-benzyl 3-(tert-butoxycarbonylamino)-4-hydroxy-4-(2,4,5-trifluorophenyl)butyrate (yield: 68%) was obtained using the same method.

Example 3

Preparation of (3S)-cyclohexyl 3-(tert-butoxycarbonylamino)-4-hydroxy-4-(2,4,5-trifluorophenyl)butyrate In accordance with the method described in Example 1, except that 29.9 g of (S)-cyclohexyl 3-(tert-butoxycarbonylamino)-4-oxo-n-butyrate was used to replace (S)-methyl 3-(tert-butoxycarbonylamino)-4-oxo-n-butyrate, 21.5 g (3S)-cyclohexyl 3-(tert-butoxycarbonylamino)-4-hydroxy-4-(2,4,5-trifluorophenyl)butyrate (yield: 71%) was obtained using the same method.

Example 4

Preparation of (3S)-methyl 3-(benzyloxycarbonyl amino)-4-hydroxy-4-(2,4,5-trifluorophenyl)butyrate 116.05 g trifluorobromobenzene and 400 ml tetrahydrofuran were added to a clean flask. The resulting mixture was cooled to −10 to −5° C., and then 864 ml (0.7 mol) methyl magnesium bromide was added thereto dropwise. The mixture was stirred for 1 hour for use. 23.5 g (S)-methyl 3-(benzyloxycarbonylamino)-4-oxo n-butyrate was dissolved in 300 ml THF, and added dropwise to the mixture mentioned above and kept at this temperature for 3 hours after completion of the addition. 400 ml solution of ammonium chloride was added dropwise. Layers were separated. The aqueous layer was extracted with tetrahydrofuran (200 ml×2). The organic layer was dried and concentrated to get 31.4 g (3S)-methyl 3-(benzyloxycarbonylamino)-4-hydroxy-4-(2,4,5-trifluorophenyl)butyrate (yield: 78.5%).

Example 5

Preparation of (3S)-benzyl 3-(benzoylamino)-4-hydroxy-4-(2,4,5-trifluorophenyl)butyrate In accordance with the method described in Example 4, except that an equal amount of benzyl lithium and 30.7 g of (S)-benzyl 3-(benzoylamino)-4-oxo-n-butyrate was used to replace methyl magnesium bromide and (S)-methyl 3-(benzyloxycarbonylamino)-4-oxo n-butyrate respectively, 21.69 g benzyl (3S)-3-(benzoylamino)-4-hydroxy-4-(2,4,5-trifluorophenyl)butyrate (yield 73.7%) was obtained using the same method.

Step a

Example 6

Preparation of (R)-methyl 3-(tert-butoxycarbonylamino)-4-(2,4,5-trifluorophenyl)butyrate To a clean autoclave, 36.3 g (3S)-3-(tert-butoxycarbonylamino)-4-hydroxy-4-(2,4,5-trifluorophenyl)n-butyl ester, 363 ml methanol and 1.8 g 5% Pd/C were added. Nitrogen replacement was performed three times. The oxygen content measured was less than 0.5%. The pressure of hydrogen gas was 0.5 Mpa. The mixture was heated to 40° C. for reaction. After 4 hours, palladium carbon was filtrated out, and the resulting mixture was concentrated under reduced pressure to obtain 26.03 g (R)-methyl 3-(tert-butoxycarbonylamino)-4-(2,4,5-trifluorophenyl)butyrate (yield: 75%).

Example 7

Preparation of (R)-benzyl 3-(tert-butoxycarbonylamino)-4-(2,4,5-trifluorophenyl)butyrate In accordance with the method described in Example 6, except that 43.94 g (3S)-benzyl 3-(tert-butoxycarbonylamino)-4-hydroxy-4-(2,4,5-trifluorophenyl)butyrate and an equal amount of anhydrous ethanol were used to replace (3S)-3-(tert-butoxycarbonylamino)-4-hydroxy-4-(2,4,5-trifluorophenyl)n-butyl ester and methanol respectively, 33.83 g (R)-benzyl 3-(tert-butoxycarbonylamino)-4-(2,4,5-trifluorophenyl)butyrate (yield: 77%) was obtained using the same method.

Example 8

Preparation of (R)-cyclohexyl 3-(tert-butoxycarbonylamino)-4-(2,4,5-trifluorophenyl)butyrate In accordance with the method described in Example 6, except that 43.14 g (3S)-cyclohexyl 3-(tert-butoxycarbonylamino)-4-hydroxy-4-(2,4,5-trifluorophenyl)butyrate and an equal amount of anhydrous ethanol were used to replace (3S)-3-(tert-butoxycarbonylamino)-4-hydroxy-4-(2,4,5-trifluorophenyl)n-butyl ester and methanol respectively, 32.82 g (R)-cyclohexyl 3-(tert-butoxycarbonylamino)-4-(2,4,5-trifluorophenyl)butyrate (yield: 79%) was obtained using the same method.

Step b

Example 9

Preparation of (R)-3-(tert-butoxycarbonylamino)-4-(2,4,5-trifluorophenyl)n-butyric acid To a clean flask, 34.73 g (R)-methyl 3-(tert-butoxycarbonylamino)-4-(2,4,5-trifluorophenyl)butyrate, 100 ml toluene, 160 ml water and 4.8 g sodium hydroxide were added. The mixture was warmed to 60° C. and kept at this temperature for 3 hours. 4.73 g hydrochloric acid was added dropwisely. After completion, the resulting mixture was kept at 20-30° C. for 2 hours and filtrated to obtain 30.66 g (R)-3-(tert-butoxycarbonylamino)-4-(2,4,5-trifluorophenyl)n-butyric acid (yield: 92%).

Example 10

Preparation of (R)-3-(tert-butoxycarbonylamino)-4-(2,4,5-trifluorophenyl)n-butyric acid To a clean flask, 34.73 g (R)-cyclohexyl 3-(tert-butoxycarbonyl amino)-4-(2,4,5-trifluorophenyl)butyrate, 300 ml water and 5.2 g potassium carbonate were added. The mixture was warmed to 60° C. and kept at this temperature for 3 hours. 4.73 g hydrochloric acid was added dropwisely. After completion, the resulting mixture was kept at 20-30° C. for 2 hours and filtrated to obtain 29.99 g (R)-3-(tert-butoxycarbonylamino)-4-(2,4,5-trifluorophenyl)n-butyric acid (yield: 90%).

Step c

Example 11

Preparation of (R)-methyl 3-(tert-butoxycarbonylamino)-4-(mesylate)-4-(2,4,5-trifluorophenyl)butyrate To a clean flask, 36.3 g (3S)-methyl 3-(tert-butoxycarbonylamino)-4-hydroxy-4-(2,4,5-trifluorophenyl)butyrate and 360 ml dichloromethane were added. The resulting mixture was cooled to −20° C. 28.59 g methanesulfonyl chloride was added dropwisely over one hour. The resulting mixture was warmed to room temperature and kept at this temperature for 2 hours. 180 ml water was added. The mixture was allowed to stand and layers were separated. The organic layer was washed twice with saturated sodium bicarbonate solution, dried and concentrated to obtain 35.6 g (R)-methyl 3-(tert-butoxycarbonylamino)-4-(mesylate)-4-(2,4,5-trifluorophenyl)butyrate (yield: 73%).

Example 12

Preparation of (R)-cyclohexyl 3-(tert-butoxycarbonylamino)-4-(p-toluenesulfonate)-4-(2,4,5-trifluorophenyl)butyrate In accordance with the method described in Example 12, except that 41.54 g (3S)-cyclohexyl 3-(tert-butoxycarbonylamino)-4-hydroxy-4-(2,4,5-trifluorophenyl)butyrate was used to replace (3S)-methyl 3-(tert-butoxycarbonylamino)-4-hydroxy-4-(2,4,5-trifluorophenyl)butyrate, and 32.1 g toluene sulfonyl chloride was used to replace methanesulfonyl chloride. 35.6 g (R)-cyclohexyl 3-(tert-butoxycarbonylamino)-4-(mesylate)-4-(2,4,5-trifluorophenyl)butyrate (yield: 70%) was obtained using the same method.

Step d

Example 13

Preparation of (R)-methyl 3-(tert-butoxycarbonylamino)-4-(2,4,5-trifluorophenyl)butyrate To a clean autoclave, 49.53 g (R)-3-(tert-butoxycarbonylamino)-4-(trifluoromethanesulfonate)-4-(2,4,5-trifluorophenyl)n-butyl ester, 363 ml methanol and 1.8 g 5% Pd/C were added. Nitrogen replacement was performed three times. The oxygen content measured was less than 0.5%. The pressure of hydrogen was 0.5 Mpa. The mixture was heated to 60° C. for reaction. After 4 h, palladium carbon was filtrated out, and the resulting mixture was concentrated under reduced pressure to obtain 26.4 g (R)-methyl 3-(tert-butoxycarbonylamino)-4-(2,4,5-trifluorophenyl)butyrate (yield: 76%).

In conclusion, the present invention relates to Sitagliptin intermediates and preparation methods and uses thereof. The methods comprises reacting a compound of formula (II) and trifluorobromobenzene with a Grignard reagent by Grignard reaction to obtain a compound of formula (I). Compound of formula (I) is a new intermediate compound for the synthesis of Sitagliptin. Compound of formula (I) can be easily used for preparing another important intermediate compound (V) for the synthesis of Sitagliptin.

It should be noted that all documents mentioned in the present invention are herein incorporated by reference, as each document is incorporated herein by reference separately. In addition, it should be understood that the description mentioned above contains the particular examples according to the present invention and the technology principle applied. Various alteration or modification can be made without departing from the spirit and scope of the present invention after those skilled in the art read the contents of the present invention, thus, such equivalent forms also fall within the scope of the present invention.

What is claimed is:

1. A compound of the following formula (I):

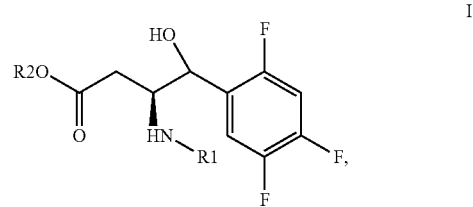

wherein R1 is R3OCO—, Pht- or R3CO—; R3 is $C_1$-$C_8$alkyl, benzyl or $C_6$-$C_{10}$aryl; R2 is $C_1$-$C_8$alkyl, benzyl or $C_6$-$C_{10}$aryl.

2. The compound according to claim 1, wherein R3 is tert-butyl, benzyl or phenyl; R1 is tert-butoxycarbonyl, benzyloxycarbonyl or benzoyl; R2 is methyl, benzyl or cyclohexyl.

3. The compound according to claim 2, selected from the groups consisting of:

methyl (3S)-3-(tert-butoxycarbonylamino)-4-hydroxy-4-(2,4,5-trifluorophenyl)butyrate;

benzyl (3S)-3-(tert-butoxycarbonylamino)-4-hydroxy-4-(2,4,5-trifluorophenyl)butyrate;

cyclohexyl (3S)-3-(tert-butoxycarbonylamino)-4-hydroxy-4-(2,4,5-trifluorophenyl)butyrate;

methyl (3S)-3-(benzyloxycarbonylamino)-4-hydroxy-4-(2,4,5-trifluorophenyl)butyrate;
benzyl (3S)-3-(benzoylamino)-4-hydroxy-4-(2,4,5-trifluorophenyl) butyrate.

4. A method for preparing the compound of formula (I) according to claim 1, comprising reacting a compound of formula (II) and trifluorobromobenzene with a Grignard reagent by a Grignard reaction to obtain a compound of formula (I):

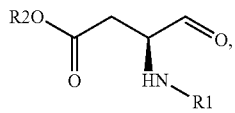

wherein, R1 and R2 have the same definitions as defined in claim 1.

5. The method according to claim 4, wherein the Grignard reagent is magnesium, lithium, (R4)2Mg, R4Li or R4MgX; wherein R4 is $C_1$-$C_8$alkyl or $C_6$-$C_{10}$aryl; and X is selected from chloro or bromo.

6. A method for preparing a compound of formula (VI) from compound of formula (I):

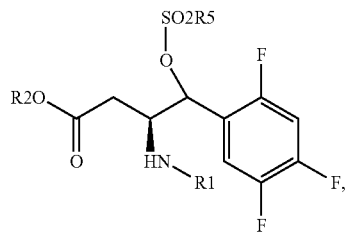

wherein, R1 and R2 have the same definitions as defined in claim 1; R5 is trifluoromethyl, C1-C8alkyl, phenyl or phenyl substituted on the para-position.

7. The method according to claim 6, characterized in that a compound of formula (I) is esterificated with $R5SO_2Cl$ to obtain a compound of formula (VI):

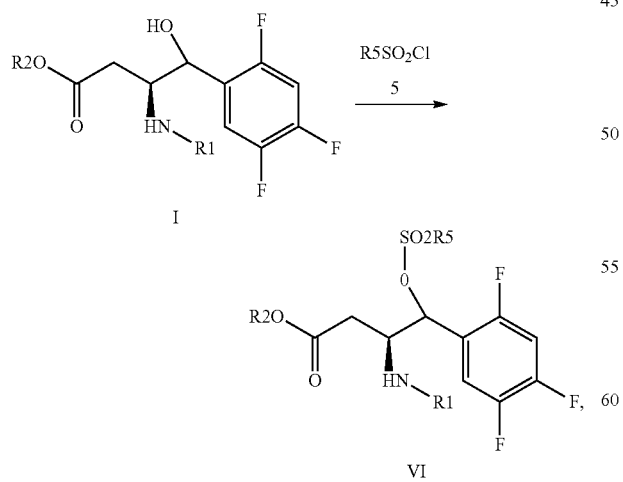

wherein R1 and R2 have the same definitions as defined in claim 1; R5 is trifluoromethyl, C1-C8alkyl, phenyl or phenyl substituted on the para-position.

8. A method for preparing a compound of formula (IV) from a compound of formula (I) according to claim 1:

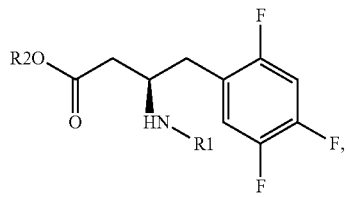

wherein R1 and R2 have the same definitions as the defined in claim 1.

9. The method according to claim 8, characterized in that the heteroatom on the benzyl group in the compound of formula (I) is removed to give a compound of formula (IV):

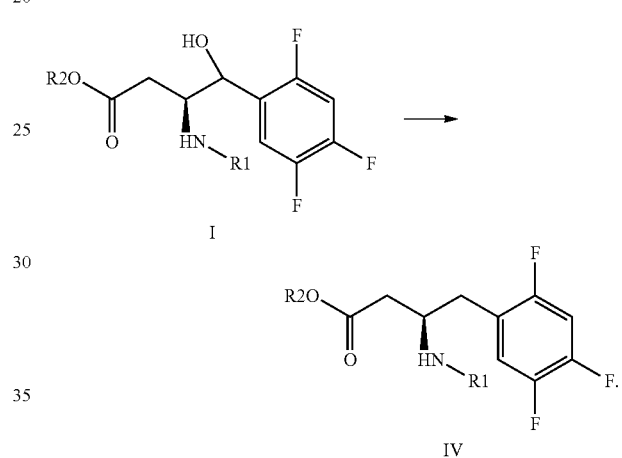

10. The method according to claim 8, characterized in that it comprises:

Step c: a compound of formula (I) is esterificated with $R5SO_2Cl$ to obtain a compound of formula (VI):

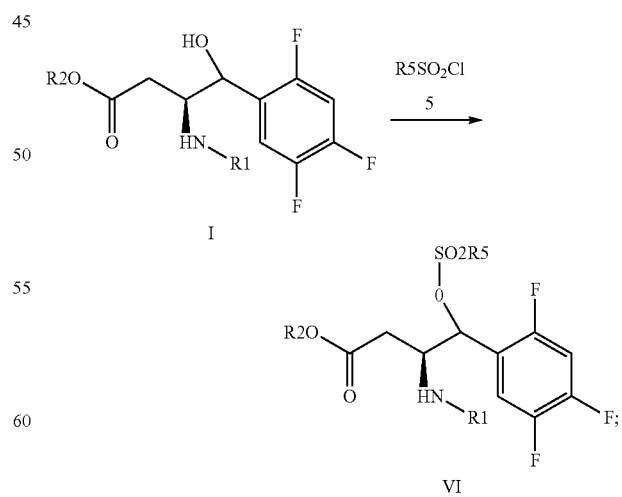

Step d: the heteroatom on the benzyl group in the compound of formula (VI) is removed to give a compound of formula (IV):

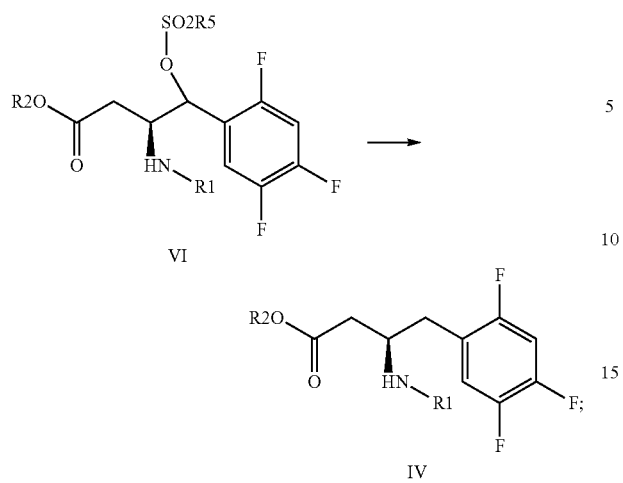

wherein R1 and R2 have the same definitions as defined in claim 1; R5 is trifluoromethyl, C1-C8alkyl, phenyl or phenyl substituted on the para-position.

11. A method for preparing a compound of formula (V) from a compound of formula (I) according to claim 1:

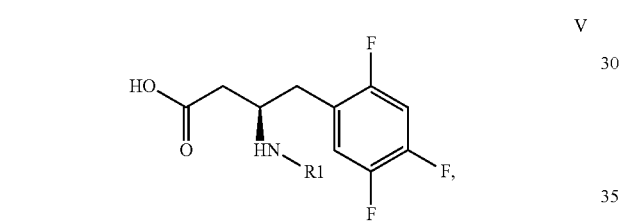

wherein R1 in the compound of formula (V) has the same meaning as defined in claim 1.

12. The method according to claim 11, comprises:

Step a: the heteroatom on the benzyl group of the compound of formula (I) is removed to obtain a compound of formula (IV):

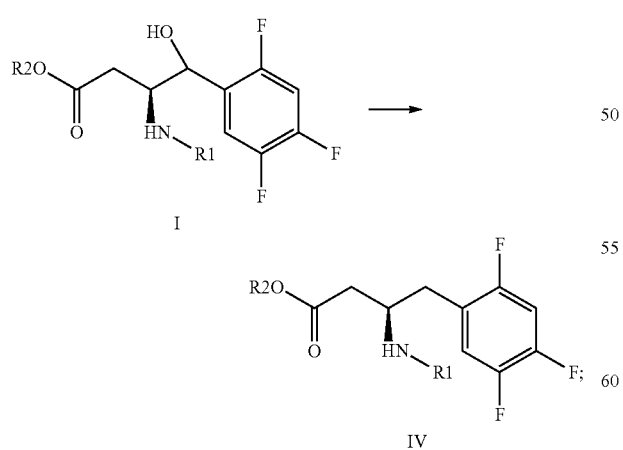

Step b: the compound of formula (IV) is subjected to a hydrolysis reaction to obtain a compound of formula (V):

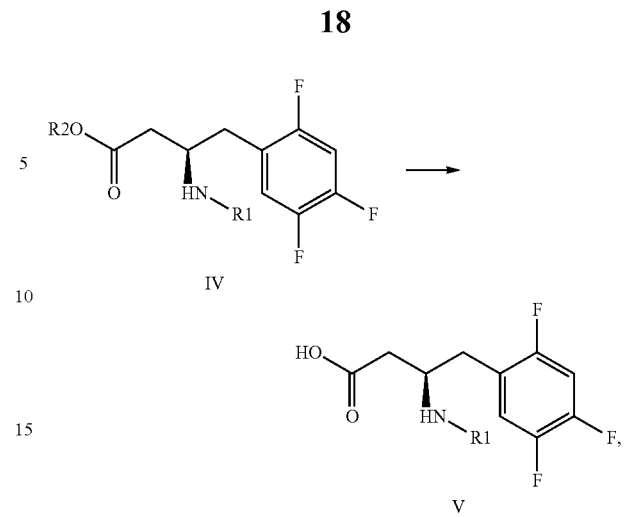

wherein R1 and R2 have the same definitions as defined in claim 1.

13. The method according to claim 11, comprises:

Step c: a compound of formula (I) is esterificated with R5SO₂Cl to obtain a compound of formula (VI):

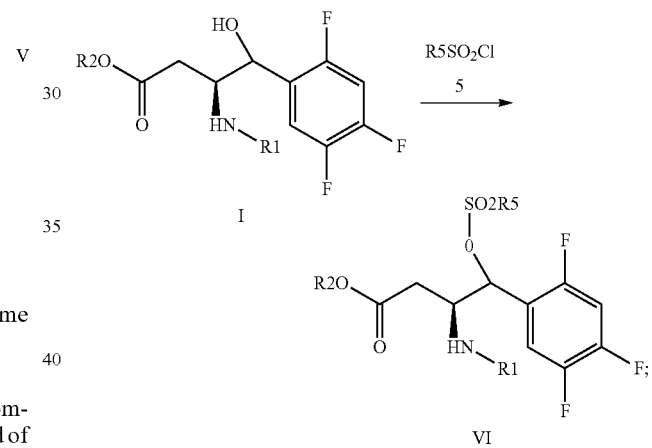

Step d: the heteroatom on the benzyl group of a compound of formula (VI) is removed to obtain a compound of formula (IV):

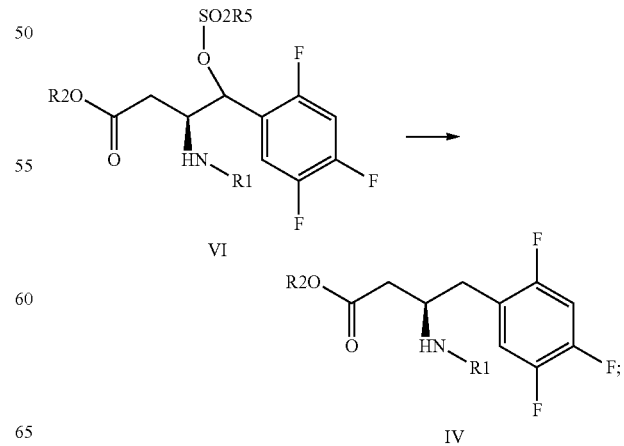

Step b: the compound of formula (IV) is subjected to a hydrolysis reaction to obtain a compound of formula (V):
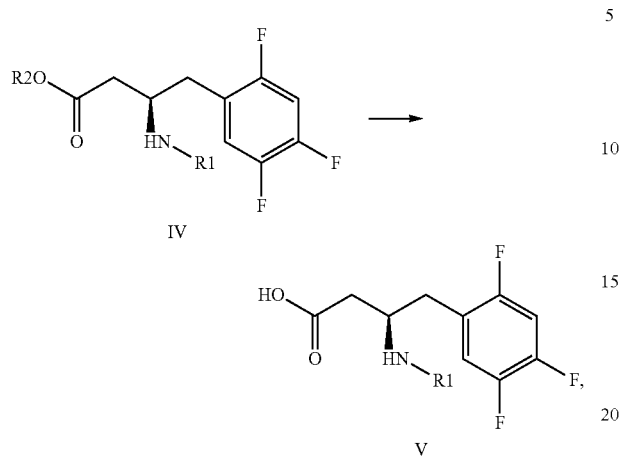
wherein R1 and R2 have the same definitions as defined in claim 1; R5 is trifluoromethyl, C1-C8alkyl, phenyl or phenyl substituted on the para-position.
* * * * *